US010967088B2

(12) United States Patent
Fudakowski (10) Patent No.: US 10,967,088 B2
(45) Date of Patent: Apr. 6, 2021

(54) METHOD OF CALCULATING AN EXPOSURE TIME FOR DISINFECTING A ROOM USING AN ULTRAVIOLET DISINFECTING APPARATUS

(71) Applicant: FINSEN TECHNOLOGIES LIMITED, London (GB)

(72) Inventor: Adam Fudakowski, London (GB)

(73) Assignee: FINSEN TECHNOLOGIES LIMITED, London (GB)

( * ) Notice: Subject to any disclaimer, the term of this patent is extended or adjusted under 35 U.S.C. 154(b) by 136 days.

(21) Appl. No.: 16/306,777

(22) PCT Filed: Jun. 13, 2017

(86) PCT No.: PCT/GB2017/051706
§ 371 (c)(1),
(2) Date: Dec. 3, 2018

(87) PCT Pub. No.: WO2017/216533
PCT Pub. Date: Dec. 21, 2017

(65) Prior Publication Data
US 2019/0160192 A1 May 30, 2019

(30) Foreign Application Priority Data
Jun. 14, 2016 (GB) .................................... 1610302

(51) Int. Cl.
*A61L 2/26* (2006.01)
*A61L 9/20* (2006.01)
*A61L 2/10* (2006.01)

(52) U.S. Cl.
CPC .................. *A61L 2/26* (2013.01); *A61L 2/10* (2013.01); *A61L 9/20* (2013.01); *A61L 2202/14* (2013.01);
(Continued)

(58) Field of Classification Search
CPC ..... A61L 2/10; A61L 2/24; A61L 2/26; A61L 9/20; A61L 2202/11; A61L 2202/14; A61L 2202/16; A61L 2202/25; A61L 2209/111
See application file for complete search history.

(56) References Cited

U.S. PATENT DOCUMENTS

| 6,656,424 B1 | 12/2003 | Deal |
| 2012/0223216 A1 | 9/2012 | Flaherty et al. |
| 2015/0069270 A1 | 3/2015 | Shur et al. |

FOREIGN PATENT DOCUMENTS

| WO | WO 2013/116566 A1 | 8/2013 |
| WO | WO 2014/088580 A8 | 6/2014 |
| WO | WO 2015/116876 A1 | 8/2015 |

OTHER PUBLICATIONS

Partial International Search Report of PCT/GB2017/051706 dated Aug. 11, 2017, 11 pages.

(Continued)

*Primary Examiner* — Timothy C Cleveland
(74) *Attorney, Agent, or Firm* — Lathrop GPM LLP (57) ABSTRACT

Method of calculating an exposure time for disinfecting a room using an ultraviolet disinfecting apparatus comprises the steps of measuring distances by: using a spatial sensor on the ultraviolet disinfecting apparatus, to perform a first scan of a boundary surface of the room, to measure a first set of distances from the sensor to the boundary surface; adjusting the height or orientation of the spatial sensor; using the spatial sensor to perform a second scan of the boundary surface of the room, to measure a second set of distances from the adjusted sensor to the boundary surface; and subsequently, calculating the exposure time in dependence the sets of distances.

9 Claims, 6 Drawing Sheets (52) U.S. Cl.
CPC ...... *A61L 2202/25* (2013.01); *A61L 2209/111* (2013.01)

(56) References Cited

OTHER PUBLICATIONS

International Search Report of PCT/GB2017/051706 dated Oct. 4, 2017, 19 pages.
United Kingdom Search Report of GB1610302.0 dated Dec. 13, 2016, 4 pages.

METHOD OF CALCULATING AN EXPOSURE TIME FOR DISINFECTING A ROOM USING AN ULTRAVIOLET DISINFECTING APPARATUS

FIELD OF THE INVENTION

The present invention relates to an ultraviolet (UV) disinfecting apparatus. More particularly, but not exclusively, the invention relates to a method of calculating an exposure time for disinfecting a room using a UV disinfecting apparatus; and to a UV disinfecting apparatus configured to calculate exposure time.

BACKGROUND OF THE INVENTION

Use of ultraviolet (UV) light for disinfection of medical equipment is known in the art. UV-C is high frequency UV radiation, which tests have shown kills all known pathogens at a wavelength between 250 and 260 nm. UV-C is suitable for air, water and surface disinfection. Apparatus for disinfecting a room using UV radiation are known.

When using a UV disinfecting apparatus to disinfect a room, it tends to be necessary to determine the dose of UV that different parts of the room have been exposed to, typically to ensure that all parts of the room have received a sufficient dose to be disinfected.

U.S. Pat. No. 6,656,424 B1 discloses a UV sterilising unit for a room, the unit having mercury bulbs to generate UV-C. A number of sensors detect the direction from which the lowest level of UV-C is reflected back to the sensors ('the darkest area'). The exposure time is determined as the time required for a bactericidal dose of UV-C to be reflected from the darkest area.

A problem with this type of method is that it may be inefficient; certain areas in the treated room receive more than the required dose in order to ensure that the darkest areas are sufficiently exposed. Moreover, the measured reflected dose may not be a sufficiently accurate proxy for the dose received at a particular location, leading to irregular or incomplete treatment.

WO2014/088580A8 discloses a system for receiving data regarding characteristics of a room in which one or more disinfection sources are arranged. The data may be received using a spatial sensor. The system determines, based on the received data, individual operating parameters for the one or more disinfection sources. Operating parameters can include run time, position, orientation of particular components, germicidal dosing parameters and power supplied.

A problem with this type of method is that the obtained data may not reflect the true characteristics of the room. For example a spatial sensor may misinterpret furniture, or other objects in the room, as being the walls of the room and therefore perceive the room to be smaller than it actually is. Alternatively or additionally, a spatial sensor may be unable to take into account the layout, proliferation or shape of furniture other objects in the room, and therefore the required exposure time may be inaccurate.

The present invention seeks to mitigate the above-mentioned problems. Alternatively or additionally, the present invention seeks to provide an improved disinfection apparatus and method of use.

SUMMARY OF THE INVENTION

According to a first aspect of the invention there is provided a method of calculating an exposure time for disinfecting a room using an ultraviolet disinfecting apparatus, the method comprising the steps of: measuring distances by: a) using a spatial sensor on the ultraviolet disinfecting apparatus, to perform a first scan of a boundary surface of the room, to measure a first set of distances from the sensor to the boundary surface; b) adjusting the height or orientation of the spatial sensor; c) using the spatial sensor to perform a second scan of the boundary surface of the room, to measure a second set of distances from the adjusted sensor to the boundary surface; and subsequently calculating the exposure time in dependence the sets of distances. The present invention recognises that by providing a first scan, and then adjusting the sensor before conducting a second scan, a more accurate estimation of the characteristics of the room may be obtained. This in turn, may enable a more accurate calculation of the correct exposure time.

Although the first aspect of the invention refers to a room, it will be appreciated that the term 'room' encompasses any space to be irradiated and may therefore include the interior of an ambulance, a cupboard, a corridor, part of a room, or other space. It will be appreciated that a boundary surface of a room is a 3-D surface and may comprise not only parts of the wall but also intervening objects attached or adjacent the wall such as furniture. It will also be appreciated that measuring distances directly may be equivalent to measuring an equivalent parameter (such as time to receive a reflected signal). A measurement of time may be used as a proxy for distance (since they are inter-related).

The first scan may be arranged such that the first set of distances is measured within a substantially horizontal plane. The second scan may be arranged such that the second set of distances is measured within a substantially horizontal plane. The first scan may be substantially parallel to the second scan. The first scan may be from a different height than the second scan. Such an arrangement has been found to be beneficial because it enables the distance to the boundary surface to be determined at two different levels within the room. This may enable (by comparing the measurements at the two levels) a more accurate determination of the likely shape of the room.

In another embodiment, the first scan may be from the same height as the second scan. The spatial sensor used to conduct the first scan may have a different orientation when it is used to conduct the second scan. The first scan may thus be angled relative to the second scan. Such an arrangement has been found to be beneficial because it may enable the distance to the boundary surface to be determined from two different orientations. This may enable (by comparing the measurements from the two levels) a more accurate determination of the likely number of obstructions (i.e. of furniture or other objects) within the room.

In a preferred embodiment of the invention, the step of measuring distances further comprises:

d) further adjusting the height or orientation of the spatial sensor; and e) using the spatial sensor to perform a third scan of the boundary surface of the room, to measure a third set of distances from the further-adjusted sensor to the boundary surface.

Conducting a third scan has the advantage of providing yet further data on the characteristics of the boundary surface. The third scan may provide a combination of the above-mentioned advantages of changing the height and orientation of the spatial sensor (i.e. it may enable a more accurate determination of the likely shape of the room and/or of the likely number of obstructions within the room).

It may be that in step b), the height of the sensor is adjusted and in step d) the orientation of the sensor is adjusted. In step b) the height of the sensor may be increased. It may be that the adjusting of the orientation of the sensor is such that the sensor is orientated downwardly towards the base of the boundary surface. Such an arrangement is beneficial because it directs the spatial sensor towards a region of the room in which there is likely to be obstructions (for example in the form of floor-standing furniture).

It may be that in step d) the orientation of the sensor is adjusted during the third scan in dependence on the rotational position of the sensor within the third scan. Thus, the angle of the sensor may be continuously adjusted as the sensor is rotated to perform a scan. Adjusting the orientation of the sensor during the scan enables a region of the room (e.g. the bottom of the room walls (the skirting-boards)) to be traced even when the sensor is not in the centre of the room. Adjusting the orientation of the sensor during the scan also provides a scan tailored to the dimensions of the room. This may be particularly advantageous if the room is an unusual, or non-uniform shape.

The orientation of the sensor may be determined by:

(i) determining, for each rotational position of the scan, the larger of the first and second distances at that corresponding rotational position;

(ii) calculating the orientation of the sensor based on the larger of the distances in step (i) and the height of the sensor. Determining the orientation in this manner, may enable the sensor to be continuously directed to a fixed level (e.g. the predicted location of the skirting board) as the scan is conducted.

The step of calculating the exposure time may comprise comparing, for each rotational position of the scan, two sets of distances to predict the distance to a wall of the room. The step of calculating the exposure time may comprise selecting the maximum distance, for each rotational position of the scan, from the two sets of distances to predict the distance to a wall of the room. Embodiments of the invention having this feature recognise that the further of the two distances most likely reaches the wall (whereas the shorter distance may reach an intervening object). The walls of the room do not necessarily define the boundary surface of the room. The walls of the room may define a maximum target volume to be irradiated.

The step of calculating the exposure time may comprise comparing, for each rotational position of the scan, two sets of distances to predict the number of obstructions within the room, and adjusting the exposure time in dependence on the number of obstructions. It may be that the number of obstructions is predicted, for each rotational position of the scan, by: determining the greater of the distances in the first and second sets of distances to obtain a predicted distance to a wall; determining the component, in the third set of distances, that is parallel to the direction in which the predicted distance to a wall is measured, and; calculating the ratio between these measurements to obtain an obstruction ratio.

It will be appreciated that an obstruction ratio is an approximation of the amount of content, or number of objects within a room. Obstructions may be typically located towards the bottom of the room.

Estimating an obstruction ratio enables the exposure time to be increased according to the number of obstructions in the room. An increase in exposure time is required because shadowed areas, caused by obstructions, take longer to irradiate than areas where there is direct line of sight to the radiation source. Such scaling may provide efficiency in time and energy of exposure. Such scaling may ensure adequate treatment of all spaces (including shaded areas) of the target volume. Such scaling may reduce unnecessary over-exposure. Such scaling may reduce costs of disinfection. The method is particularly effective if the objects in a room are approximately uniformly distributed in the room.

It may be that the method comprises the step of transmitting the sets of distances to a processing module, the processing module being configured to calculate the exposure time in dependence on those distances. It may be that the method further comprises the steps of: displaying, on a graphical user interface, the region that would be disinfected if the ultraviolet disinfecting apparatus were run for the calculated exposure time; allowing a user to adjust the radius of the region to be disinfected; and calculating a new exposure time to reflect the adjustment made.

It may be that the new exposure time is calculated by adjusting the previously-calculated exposure time in proportion to the square of the adjustment in radius.

Such further steps provide the benefit of increased remote operator control. Calculating a new exposure time in proportion to the square of the adjustment in radius obviates the need for further detailed calculation using the above-detailed methodology. Calculating a new exposure time in proportion to the square of the adjustment in radius provides efficiency of processing power whilst allowing some operator control.

It will be appreciated that exposure time is intrinsically linked to the dose and to radiation intensity. In that sense, the terms are interchangeable in this context.

A predetermined limit may be applied to the measured distance, such that where a measured distance exceeds the predetermined limit, the measured distance is replaced by that predetermined limit. It may be that the predetermined limit is less than 15 metres. It may be that the predetermined limit is between 8 to 12 metres. It may be that the operator can adjust the predetermined limit according to the size of the particular room to be treated. Setting a predetermined limit avoids distortion of the exposure time calculation due to long distances measured through open windows, doors, hallways or other apertures in the room.

It may be that the method comprises the step of scaling the disinfection time according to the UV-C output intensity. The UV-C intensity may be measured using photo-detectors and compared to the known values of the tubes when they were new. Such a step allows a more accurate disinfection time to be calculated, allowing for a longer exposure as the tubes age and UV-C intensity reduces.

According to a second aspect of the invention there is provided a method of disinfecting a room including the steps of: determining the exposure time according to the first aspect, and irradiating the room with ultraviolet radiation for the exposure time.

According to yet another aspect of the invention, there is provided an ultraviolet disinfecting apparatus for conducting the above mentioned method. The apparatus may comprise: a spatial sensor configured to perform a first scan of a boundary surface of the room, to measure a first set of distances from the sensor to the boundary surface; wherein the apparatus is configured such that the height or orientation of the spatial sensor is adjustable such that the spatial sensor can perform a second scan of the boundary surface of the room, to measure a second set of distances from the adjusted sensor to the boundary surface.

The apparatus may have a first unit having a first UV emitter and a second unit having a second UV emitter wherein the second unit is movable relative to the first unit from an un-extended position in which the first and second units at least partially overlap, to an extended or super-extended position, wherein in the un-extended position the first UV emitter is at least partially exposed to emit UV radiation. Such an arrangement is especially beneficial as it facilitates a straightforward way of adjusting the height of the sensor, whilst obtaining the complementary benefits of mitigating the existence of shadows by adjusting the height of the UV emitters.

The apparatus may be configured such that the height or orientation of the spatial sensor is further adjustable such that the spatial sensor can perform a third scan of the boundary surface of the room, to measure a third set of distances from the further adjusted sensor to the boundary surface.

The apparatus may further comprise a processing module. The processing module may be configured to calculate an exposure time in dependence on the differences between the measured distances.

The apparatus may comprise a graphical user interface (GUI). The GUI may be configured to display the boundary surface of the room in dependence on the measured distances, and to display a disinfection region based on the exposure time. The apparatus may be configured so that the size of the disinfection region may be adjusted using the graphical user interface.

The processing module may be configured to calculate a new exposure time to reflect the adjustment made to the size of the disinfection region.

The apparatus may be generally upright having a vertical axis around which a plurality of UV light sources are arranged. The spatial sensor may be positioned co-axially with the vertical axis such that it is in a central location relative to the light sources. The spatial sensor may be in a sensor head.

The spatial sensor may be arranged to determine distances using an optical distance-measuring module. The spatial sensor may comprise an emitter and receiver.

The spatial sensor may be rotatable throughout a horizontal plane. The spatial sensor may be rotatable by over 360 degrees, for example by 400 degrees, in the horizontal plane.

The orientation of the spatial sensor may be adjustable above below a central horizontal plane. The orientation of the spatial sensor may be adjustable up to 90 degrees above the central horizontal plane. The orientation of the spatial sensor may be adjustable up to 90 degrees below the central horizontal plane.

The height of the spatial sensor is adjustable by virtue of a telescopic extension/retraction of the disinfecting apparatus.

According to yet another aspect of the invention, there is provided a method of monitoring failure of an ultraviolet (UV) emitter in a UV disinfecting apparatus comprising a plurality of UV emitters, the method including the steps of:
sequentially energising one or more of the UV emitters and after each energisation:
measuring the current delivered to the UV emitter(s); and
comparing the current delivered to an expected reference value; and
identifying failure of one of the UV emitters when the combined current is different to the expected reference value.

According to yet another aspect of the invention, there is provided an apparatus for conducting the above mentioned method. The apparatus may comprise plurality of UV emitters and a current control and monitoring module, the current control and monitoring module being configured to:
sequentially energise each of the UV emitters and after each energisation:
measure the current delivered to the UV emitter(s); and
compare the current delivered to an expected reference value; and
identify failure of one of the UV emitters when the combined current is different to the expected reference value.

The apparatus may have a dual-voltage AC-DC adaptor. The apparatus may be suitable for use at mains voltage of 110V and 230V. The apparatus may be configured to fire fewer light sources at 110V than at 230V.

It will of course be appreciated that features described in relation to one aspect of the present invention may be incorporated into other aspects of the present invention. For example, the method of the invention may incorporate any of the features described with reference to the apparatus of the invention and vice versa.

DESCRIPTION OF THE DRAWINGS

An embodiment of the present invention will now be described by way of example only with reference to the accompanying schematic drawings of which.

DETAILED DESCRIPTION

Figure 1:
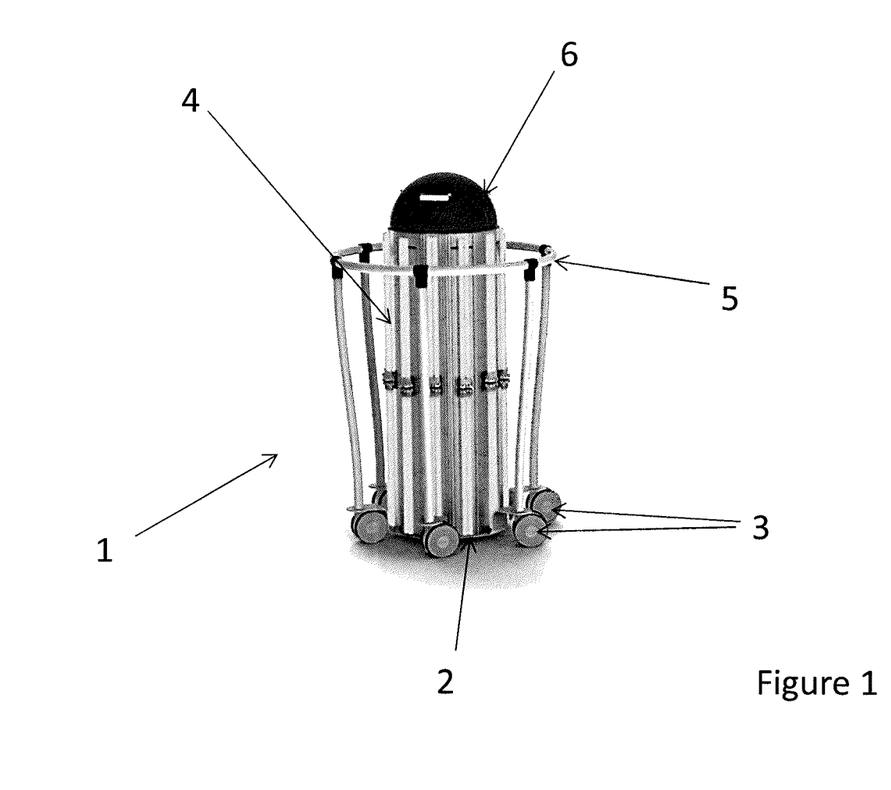
FIG. 1 is a front view of an ultraviolet disinfecting apparatus, in an un-extended configuration, according to the first embodiment of the invention.

FIG. 1 shows the ultraviolet disinfecting apparatus 1 of a first embodiment of the invention. The apparatus 1 has an upright resting position and is approximately cylindrical in shape. The apparatus 1 has two units which interlock, the upper unit being vertically extendible away from the lower unit. FIG. 1 shows the apparatus 1 in an un-extended configuration.

The apparatus 1 has a dual-voltage AC-DC adaptor suitable for use at mains voltage of 110V and 230V. The apparatus 1 incorporates known safety features such as emergency stop buttons, but otherwise is controlled remotely.

The lower unit has a bottom circular plate 2, resting on six castor wheels 3. The bottom plate 2 supports 12 UV-C tube bulbs 4, each 95 W, which extend up, and are spaced circumferentially around the edge of the bottom plate 2. Located radially inwards of the UV-C tube bulbs 4, are twelve ballasts. Also located radially inwards of the UV-C tube bulbs 4 and mounted on the bottom plate 2, are the system electronics and a linear actuator for raising the upper unit of the apparatus 1 and a photodetector for monitoring UV-C output. Fixed to the outside of the UV-C tubes 4 are passive infra-red sensors for detecting movement in the vicinity.

Around the outside of, and spaced apart from the UV-C tubes 4 of the lower unit, is a metal frame 5, supported by legs which extend down to the castor wheels 3. The metal frame 5 has a circular rim, at hand height, and allows for an operator to push the apparatus 1 on the castor wheels 3.

The upper unit, mounted on the linear actuator, has a further 12 UV-C tube bulbs, each 95 W, arranged circumferentially to interlock with the tubes of the lower unit. The spaces between the UV-C tubes 4 of the lower unit act as guide tubes for the inter-locking UV-C tubes, which slot into position adjacent the UV-C tubes 4. Mounted on the upper unit is an ultrasound distance sensor for measuring vertical height to the ceiling.

Figure 2:
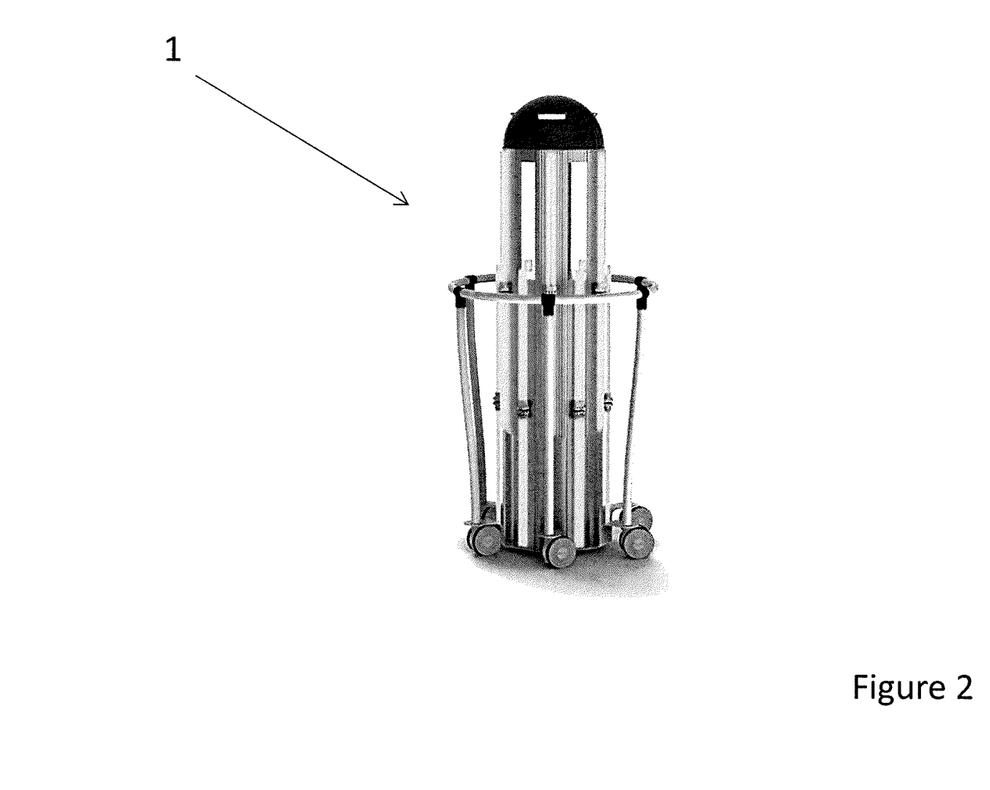
FIG. 2 is a front view of an ultraviolet disinfecting apparatus, in an extended configuration, according to the first embodiment of the invention.
Figure 3:
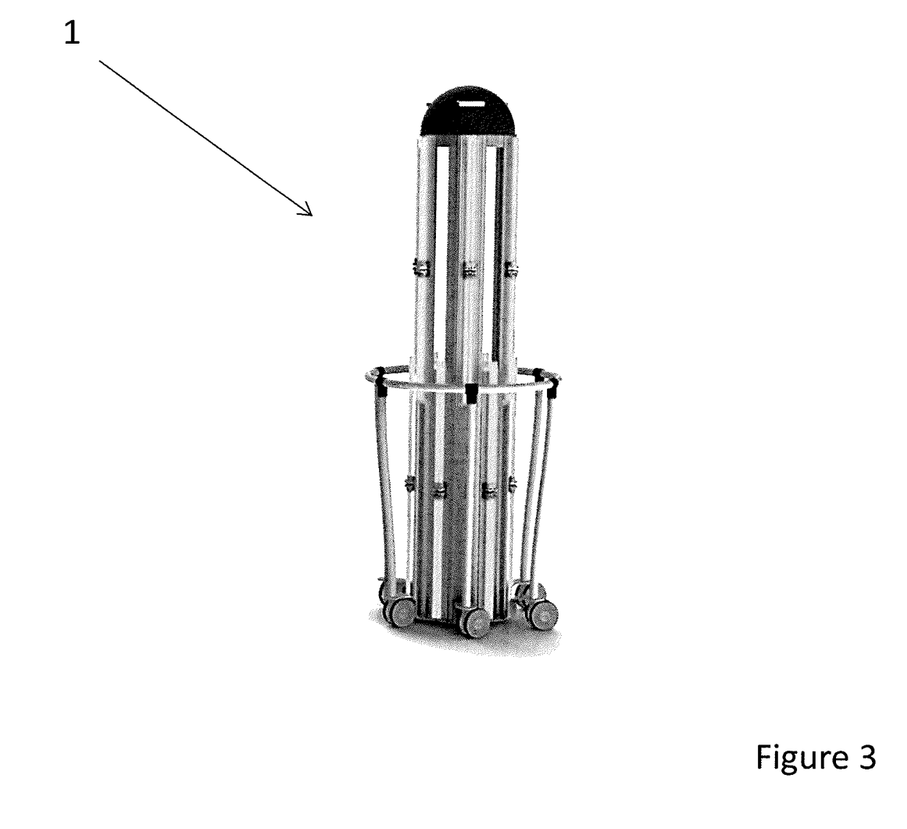
FIG. 3 is a front view of an ultraviolet disinfecting apparatus, in a super-extended configuration, according to the first embodiment of the invention.

FIG. 2 shows the same apparatus 1 in an extended configuration, with a region of partial overlap (approximately one third of the height in this configuration) between the two sets of UV-C tubes. FIG. 3 shows the same apparatus 1 in a super-extended configuration, with only a small region of overlap between the two sets of UV-C tubes.

Some of the features described above, such as the extendable nature of the apparatus, are already shown in WO 2011/055140 A1 and are not described in further detail. However, the first embodiment of the invention comprises several, additional, novel and inventive features as described in more detail below.

On top of the upper unit is a hemispherical sensor head assembly 6. The head assembly 6 comprises a hemispherical cover, surrounding an optical distance-measuring module (for measuring distance). The optical distance-measuring module comprises an emitter and receiver and functions as a spatial sensor (typically referred to herein as the 'sensor'). The sensor is rotatable through 400 degrees in a horizontal plane and, can tilt up to 90 degrees above and below its central horizontal position. The rotational resolution is 1.8 degrees, and the vertical tilt resolution is 5 degrees. The optical distance measuring module operates at resolutions typical in the industry.

The apparatus of the first embodiment of the invention has an accompanying remote tablet controller. With the exception of the execution of the process described below, the tablet itself is a conventional tablet device and is therefore not described in detail herein. The tablet communicates bi-directionally with the disinfection apparatus via a Wi-Fi network and enables the operator to operate the apparatus in manual mode, or alternatively, run an automated cycle.

In the first embodiment of the invention, the tablet is programmed to calculate an optimal disinfection time when the apparatus 1 is used in automated mode. The method of calculating that disinfection time is summarised in FIG. 4, to which reference is now made.

Description of the First Embodiment of Invention

Figure 4:
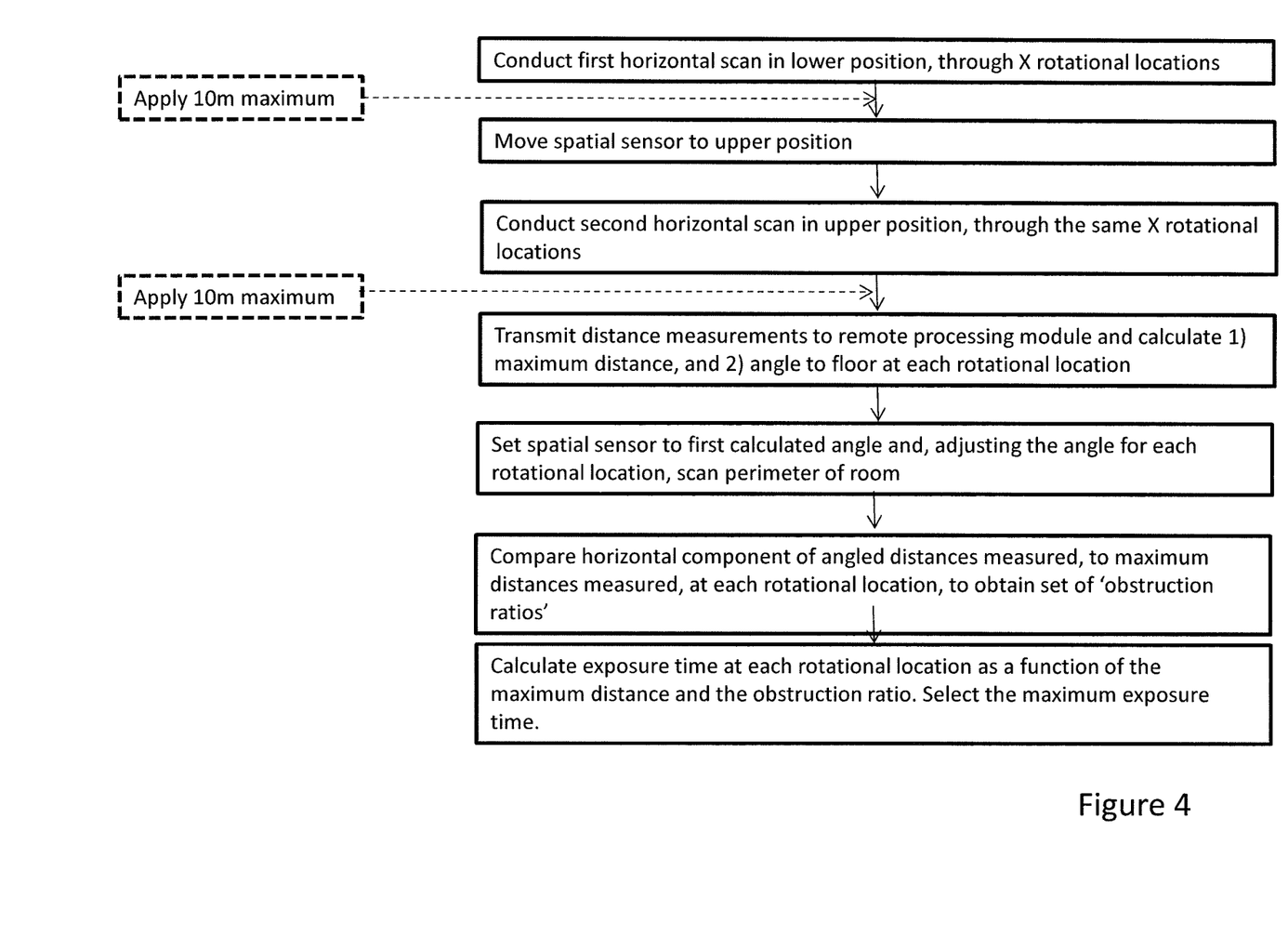
FIG. 4 is a display of the graphical user interface, according to the first embodiment of the invention.

The method has the following steps:

a) Firstly, the apparatus 1 is positioned in a room to be disinfected, in the un-extended configuration.

b) Next, a first horizontal optical scan is performed, obtaining multiple distance measurements from the sensor to the boundary of the room. To do this, the sensor rotates through 360 degrees, approximately 1.8 degrees at a time, taking distance measurements as it does so. It will be appreciated that in this context, the measured 'boundary of the room' need not necessarily be the wall of the room. For example, at the height of the first scan, there may be furniture, such as cupboards, tables or drawers protruding from the wall of the room, which the sensor will detect as being the boundary of the room (those being the first objects the sensor detects as it scans around the height of the room).

c) Next, the upper unit of the apparatus 1 is raised. The ultrasound detector sends vertical height measurements to the tablet controller, which is programmed to cease raising if the apparatus 1 extends within a predetermined distance from the ceiling.

d) A second horizontal optical scan is then performed, obtaining multiple distance measurements from the sensor to the boundary of the room, at this increased height. The scan is taken at the same rotational locations, through 360 degrees.

e) Distance measurements are then sent to the tablet controller. The controller is programmed to select and store the maximum distance measurement at each rotational location (max horizontal distance to boundary$_{loc}$), whilst applying an upper limit of 10 metres to each measurement to prevent spurious results from features such as windows or long corridors (see further details below).

f) Next, the tablet controller is programmed to calculate an angle for each rotational location, corresponding to the estimated angle at which the sensor should be directed in order to point at the junction between the wall and the floor. The angle is estimated by using the maximum horizontal distance measured (at each rotational location) and the height of the sensor from the floor, namely:

angle$_{loc}$=arctan(max horizontal distance to boundary$_{loc}$/height of the sensor from the floor)

g) The sensor head 6 orientation is adjusted to correspond to the first calculated angle and a third optical scan is performed, wherein the sensor head 6 orientation is adjusted at each rotational location of the scan to match the calculated angle (angle$_{loc}$). The third scan measures the diagonal distance (i.e. inclined at the calculated angle below the horizontal) from the sensor to the boundary of the room. As with the first and second scans, the detected boundary is not necessarily the true junction between the wall and the floor. Where objects, such as furniture are present, the third scan will typically measure a distance to those objects, therefore giving a smaller measurement than the true distance to the wall/floor junction.

h) Once the third scan is completed, the distance measurements are sent to the tablet controller.

i) The tablet controller then calculates the ratio between the horizontal component of the measured diagonal distance (i.e. (obstruction scan distance$_{loc}$*cos (angle$_{loc}$)) and the maximum horizontal distance previously calculated (i.e. max horizontal distance to boundary$_{loc}$), for each rotational location, obtaining a set of 'obstruction ratios':

obstruction ratio$_{loc}$=(obstruction scan distance$_{loc}$*cos (angle$_{loc}$))/(max horizontal distance to boundary$_{loc}$)

The calculation is such that if no objects obstruct the angled beam during the obstruction scan in a particular direction, the obstruction ratio in that direction will be one. The benefits of measuring such a ratio are discussed in further detail below.

j) The tablet controller is programmed to calculate a disinfection time, for each rotational location, using pre-stored data from look-up tables, and dependent on the maximum distances previously calculated and the obstruction ratios calculated:

time$_{loc}$=$K$*LUT$_1$[intensity]*LUT$_2$[distance]/LUT$_3$[obstruction ratio]

where:
- K=constant (scaling factor)
- $LUT_1$=Look-up table 1 indexed by estimated UV-C intensity (%)
- $LUT_2$=Look-up table 2 indexed by distance to wall
- $LUT_3$=Look-up table 3 indexed by obstruction ratio.

k) The maximum of the calculated disinfection times, from all the rotational locations of the scans, is selected. A 'warm-up' time is then added to allow the UV-C tube bulbs to reach full output. The warm-up time is calculated by measuring the UV-C output intensity using the photo-detectors and setting the 'warm-up' time to be equal to the time needed to measure an intensity of at least 80% of the expected intensity for a new bulb.

Advantages Provided by First Embodiment of Invention

Steps a) to e) enable a better estimate of the room outline to be obtained compared to only conducting one scan at one level. This is particularly necessary in a crowded space, for example an ambulance or medical treatment room, where cupboards or other objects may distort the measurements at any single chosen height (providing artificially low readings compared to if the obstructions were not there). This is important when a room has a non-uniform vertical profile, for example, when cupboards are fitted low, or high in the room, but not both.

Applying an upper limit of 10 m to each measurement ensures that the measurements of the room outline are not distorted by readings obtained through an open window, doorway, corridor, or other aperture in the room. Compared to prior art methodology therefore, the delivered dose will more accurately reflect the real room dimensions. Disinfection will be more thorough.

Steps f) to i) enable an estimate of the content (or obstructions) of the room to be obtained. Thus, the disinfection time can be increased to account for obstructions in the room in proportion to the number of obstructions. The present invention recognises that it is beneficial to account for obstructions in a room, as this ensures adequate exposure of all areas including shadowed areas. The present invention further recognises that disinfection time can be scaled in proportion to the number of obstructions in the room, by conducting an angled scan. Hence, compared to prior art methodology, disinfection is more thorough whilst not compromising efficiency. The present invention recognises that a balance must be obtained between conducting further scans to obtain more accurate room characteristics, and running a quick and cost-effective disinfection cycle.

Steps j) to k) represent a workable method for calculating disinfection time using pre-stored values in look-up tables as a function of the measured distances.

Description of Further Features in the First Embodiment of the Invention

Figure 5:
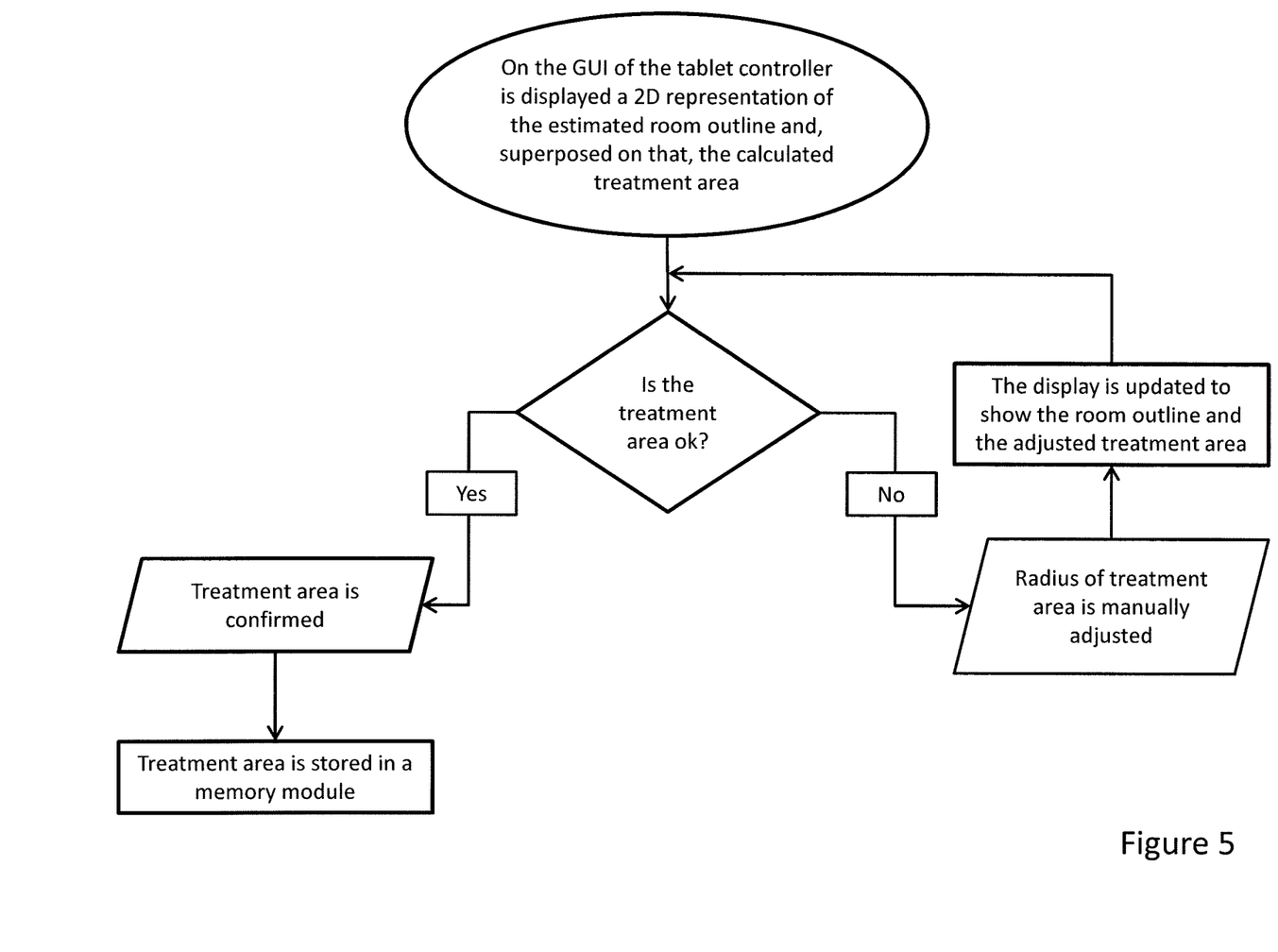
FIG. 5 is a flow diagram representing the methodology of the first embodiment of the invention.

In the first embodiment of the invention, the disinfection time calculated may be adjusted by the operator, when the apparatus 1 is used in automated mode. The method of executing such an adjustment to the disinfection time is summarised in FIG. 5, to which reference is now made. The method has the following steps:

l) The tablet displays, on the graphical user interface, a 2-D representation of the estimated room outline based on the measured distances, oriented to north, and the treatment area corresponding to the calculated maximum disinfection time superposed on the room outline.

m) The operator confirms the treatment area, or adjusts the radius directly via the graphical user interface.

n) If the treatment area is adjusted, the tablet controller is programmed to calculate a revised disinfection time, scaling the disinfection time by the square of the change in treatment radius.

o) If required, the tablet displays an updated treatment area superposed on the room outline.

p) The treatment area is stored in a memory module to log the area that can be considered as having been disinfected.

Figure 6:
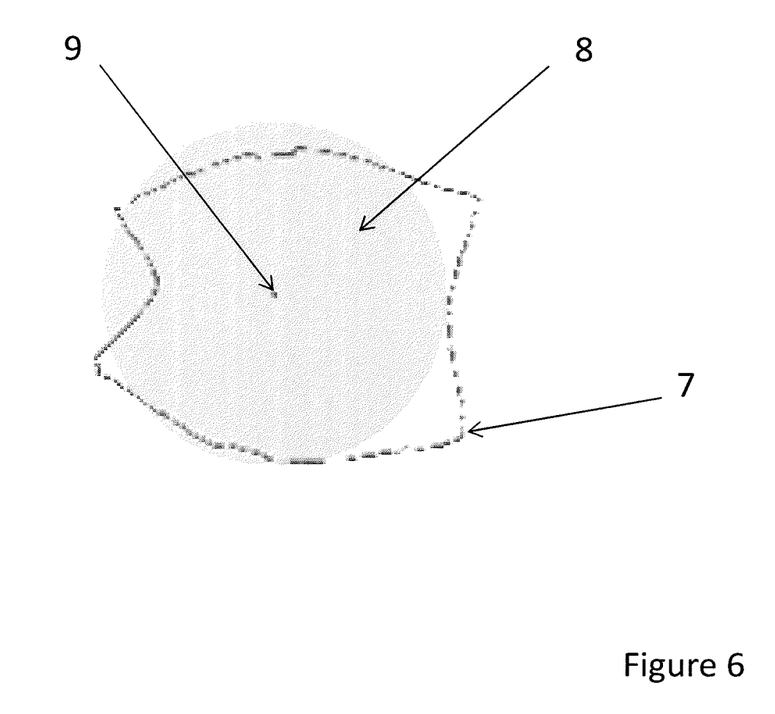
FIG. 6 shows an example display of a remote tablet controller in step 1 in FIG. 5.

FIG. 6 shows an example display of the remote tablet controller according to step l). FIG. 6 shows a room outline 7, as calculated based on measurements taken by the optical distance measuring module (see description below for more details), and superposed on that, a circular treatment area 8 (see description below for more details). The display also shows the location 9 of the apparatus 1, being at the centre of the treatment area 8.

Advantages Provided by the Further Features of the First Embodiment of the Invention Steps l) to p) represent the machine-operator interface of the system. The invention recognises that it is beneficial to allow some user control whilst maintaining an efficient automated process. These further steps allow the operator to override the recommended area, if, for example, it would be more efficient to conduct several cycles rather than one long-cycle, or more efficient to move the apparatus and calculate a new treatment area. If the room geometry is narrow, or otherwise irregular, such operator control is particularly beneficial.

Description and Advantages of Other Embodiments of the Invention

In a second embodiment of the invention (not shown), the method of calculating exposure time is as described above with reference to the first embodiment, and subsequently, the room is irradiated with UV-C radiation for the disinfection time corresponding to that required to dose the selected treatment area. In this second embodiment, the tablet is programmed to display error and warnings messages to the operator during operation. Such messages alert the user to a system fault, for example when measured UV-C light output is zero, when the tablet cannot communicate with the tower, when there is mechanical failure of the apparatus or when the warm-up time exceeds an expected level. In this second embodiment the passive infra-red sensors monitor movement during irradiation and the cycle is halted if movement is detected. Such a feature is known in the art and not discussed in detail herein. The entire process can then be repeated at a second location within the room, if required. The apparatus 1 is moved manually to the desired location and a new disinfection time is calculated.

In another embodiment of the invention (not shown), the method of calculating exposure time is as described above with reference to the first or second embodiments, but also includes the step of monitoring movement using the passive infra-red sensors during scanning and/or movement of the apparatus or sensor head, and halting the cycle if movement is detected. If movement is detected whilst the apparatus is scanning, the cycle is aborted. If movement is detected whilst the apparatus is being raised or whilst the orientation of the sensor head is adjusted, the cycle is paused and can be restarted upon operator command. The pause/re-start feature provides a safety mechanism, and provides the additional benefit of being energy-saving compared to a complete shut-down.

In another embodiment of the invention (not shown), the method of calculating exposure time is as described above with reference to any previous embodiment, but also includes the step of sequentially firing the UV-C tube bulbs, and monitoring the increments of current drawn to the ballasts, to determine whether the tubes are functioning correctly. A first pair of UV-C tubes is initiated, and current drawn to the ballasts is measured via a current monitoring module placed between the ballasts and bulbs. The tablet controller is programmed firstly, to check that current is drawn to the expected ballasts. This provides assurance that the UV-C tubes have not failed completely. The tablet controller is programmed secondly, to check the level of current drawn by each of the ballasts against an expected reference value. This provides assurance that the UV-C tubes are functioning correctly. A second pair of UV-C tubes is then initiated and checks are performed to determine whether current is being drawn to the ballasts and whether the expected increase in current drawn is consistent with expected reference values. Similar checks are performed for each of the remaining pairs of tubes. If the current is less than expected, an error message is issued. Such checks provide the benefit of reducing risk of inadequate disinfection, due to failed UV-C tubes. In this embodiment the tablet controller is programmed to alert the operator in the event of a tube failure before or during irradiation.

In another embodiment (not shown) the method of calculating exposure time is as described above with reference to any previous embodiment, but also includes the step of scaling the disinfection time according to the UV-C output intensity. The UV-C intensity can be measured using the photo-detectors and compared to the known values of the tubes when new. This step allows a more accurate disinfection time to be calculated, allowing for a longer exposure as the tubes age and UV-C intensity reduces.

Whilst the present invention has been described and illustrated with reference to particular embodiments, it will be appreciated by those of ordinary skill in the art that the invention lends itself to many different variations not specifically illustrated herein. By way of example only, certain possible variations will now be described.

It may be that the apparatus 1 of the present invention is provided in combination with satellite emitters. It may be that the tablet controller could have intelligent placement capability, for determining an optimal location, or set of locations, to position the apparatus 1 within the room, based on the measured data. The method could include additional horizontal or angled scans to better determine the outline of the room and/or the number of obstructions in the room. The sensor head 6 could include a camera for better determination of the room size and content. The tablet controller could be programmed to calculate accumulated dose within the room by summing the dose delivered from multiple treatments at different positions in the room. The system could incorporate more advanced movement detection for example ultrasound in conjunction with infra-red detection. The graphical user interface could display estimated dose received at a number of locations in the room.

Where in the foregoing description, integers or elements are mentioned which have known, obvious or foreseeable equivalents, then such equivalents are herein incorporated as if individually set forth. Reference should be made to the claims for determining the true scope of the present invention, which should be construed so as to encompass any such equivalents. It will also be appreciated by the reader that integers or features of the invention that are described as preferable, advantageous, convenient or the like are optional and do not limit the scope of the independent claims. Moreover, it is to be understood that such optional integers or features, whilst of possible benefit in some embodiments of the invention, may not be desirable, and may therefore be absent, in other embodiments.

The invention claimed is:

1. A method of calculating an exposure time for disinfecting a room using an ultraviolet disinfecting apparatus, the method comprising the steps of:
   measuring distances by:
   a) using a spatial sensor on the ultraviolet disinfecting apparatus, to perform a first scan of a boundary surface of the room, to measure a first set of distances from the sensor to the boundary surface;
   b) adjusting the height of the spatial sensor;
   c) using the spatial sensor to perform a second scan of the boundary surface of the room, to measure a second set of distances from the adjusted sensor to the boundary surface;
   d) further adjusting the orientation of the spatial sensor; and
   e) using the spatial sensor to perform a third scan of the boundary surface of the room, to measure a third set of distances from the further-adjusted sensor to the boundary surface;
   and subsequently calculating the exposure time in dependence on the sets of distances.

2. A method according to claim 1, wherein the first scan is arranged such that the first set of distances is measured within a substantially horizontal plane.

3. A method according to claim 1, wherein the second scan is arranged such that the second set of distances is measured within a substantially horizontal plane.

4. A method according to claim 1, wherein the adjusting of the orientation of the sensor is such that the sensor is orientated downwardly towards a base of the boundary surface.

5. A method according to claim 1, wherein in step d) the orientation of the sensor is adjusted during the third scan in dependence on a rotational position of the sensor within the third scan.

6. A method according to claim 5, wherein the orientation of the sensor is determined by:
   (i) determining, for each rotational position of the third scan, the larger of the first and second distances at that corresponding rotational position;
   (ii) calculating the orientation of the sensor based on the larger of the distances in step (i) and the height of the sensor.

7. A method according to claim 1, wherein the step of calculating the exposure time comprises comparing, for each rotational position of the spatial sensor during the plurality of scans, two sets of distances to predict the distance to a wall of the room.

8. A method according to claim 1, wherein the step of calculating the exposure time comprises comparing, for each rotational position of the spatial sensor during the plurality of scans, two sets of distances to predict a number of obstructions within the room, and adjusting the exposure time in dependence on the number of obstructions.

9. A method of disinfecting a room including the steps of:
   determining the exposure time according to the method of claim 1, and
   irradiating the room with ultraviolet radiation for the exposure time.

* * * * *